United States Patent
Huber et al.

[11] Patent Number: 6,132,411
[45] Date of Patent: *Oct. 17, 2000

[54] ABSORBENT ARTICLE WITH MULTIPLE ZONE SIDE PANELS

[75] Inventors: Michael T. Huber; Sheila S. Rodriguez, both of Cincinnati, Ohio

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/869,195

[22] Filed: Jun. 4, 1997

[51] Int. Cl.⁷ ..................................... A61F 13/15
[52] U.S. Cl. ................. 604/385.29; 604/385.3; 604/389; 604/391
[58] Field of Search ................... 604/358, 373, 604/385.1, 385.2, 386, 389

[56] References Cited

U.S. PATENT DOCUMENTS

| | | | |
|---|---|---|---|
| 5,151,092 | 9/1992 | Buell et al. | 604/385.2 |
| 5,358,500 | 10/1994 | Lavon et al. | 604/385.2 |
| 5,518,801 | 5/1996 | Chappell et al. | 601/385.2 |
| 5,554,165 | 9/1996 | Roe et al. | 604/385.2 |
| 5,669,897 | 9/1997 | Lavon et al. | 604/373 |
| 5,899,895 | 5/1999 | Robles et al. | 601/385.2 |

FOREIGN PATENT DOCUMENTS

| | | |
|---|---|---|
| 0547497 | 6/1993 | European Pat. Off. . |
| 5-65321 | 8/1993 | Japan . |

*Primary Examiner*—John G. Weiss
*Assistant Examiner*—K. M. Reichle
*Attorney, Agent, or Firm*—Steven W. Miller; Kevin C. Johnson; Jacobus C. Rasser

[57] ABSTRACT

Absorbent articles such as disposable diapers, incontinence briefs, diaper holders, training pants, feminine hygiene garments and the like, that have a unique side panel improves the overall fit of the absorbent article as well as reducing the red marking of the wearer's skin. Such absorbent articles include a chassis assembly preferably having a liquid pervious topsheet, a liquid impervious backsheet joined to the topsheet, and an absorbent core positioned between the topsheet and the backsheet; a pair of side panels joined to the chassis assembly; and a closure system for maintaining the absorbent article on the wearer. The side panels have a low extension force leg zone and a high extension force waist zone.

16 Claims, 4 Drawing Sheets

ABSORBENT ARTICLE WITH MULTIPLE ZONE SIDE PANELS

FIELD OF THE INVENTION

The present invention relates to absorbent articles such as diapers, incontinence briefs, training pants, and the like, and more particularly, to absorbent articles having a multi-zoned side panel providing improved fit about the wearer as well as improved comfort for the wearer.

BACKGROUND OF THE INVENTION

Infants and other incontinent individuals wear absorbent articles such as diapers to receive and contain urine and other body exudates. Absorbent articles function both to contain the discharged materials and to isolate these materials from the body of the wearer and from the wearer's garments and bed clothing. Disposable absorbent articles having many different basic designs are known to the art. For example, U.S. Pat. No. Re. 26,152, entitled "Disposable Diaper" issued to Duncan and Baker on Jan. 31, 1967, describes a disposable diaper which has achieved wide acceptance and commercial success. U.S. Pat. No. 3,860,003, entitled "Contractable Side Portions For Disposable Diaper", issued to Buell on Jan. 14, 1975, describes an elasticized leg cuff disposable diaper which has achieved wide acceptance and commercial success.

Disposable diapers with side stretch features have used stretch and force profiles that are compromise solutions to good initial fit, good sustained fit, and low degrees of red marking of the wearer's skin. The need for compromise solutions is the result of a design flaw in current stretch diapers. The design flaw is the use of a diaper-to-stretch feature bond or connection that is parallel to the longitudinal edges or machine direction edges of the diaper. The bond extending parallel to the longitudinal edges of the diaper causes forces to be very similar or equal along the stretch panel from top to bottom when the diaper is applied on a wearer. The equal forces result in either red marking of the skin at the top of the leg, poor sustained fit about the waist, or both.

Therefore, it is an object of the present invention to provide a disposable absorbent article such as a disposable diaper having improved initial fit, improved sustained fit, and reduced red marking of the wearer's skin.

It is a further object of the present invention to provide an absorbent article having a unique side panel feature.

These and other objects of the present invention will be more readily apparent when considered in reference to the following description and when taken in conjunction with the accompanying drawings.

SUMMARY OF THE INVENTION

The present invention provides absorbent articles such as disposable diapers, incontinence briefs, diaper holders, training pants, feminine hygiene garments and the like, that have a side panel that improves the initial fit and the sustained fit of the absorbent article on the wearer and a reduced redmarking of the wearer's skin. Such absorbent articles comprise a chassis assembly having end edges and longitudinal edges. The chassis assembly preferably comprises a liquid pervious topsheet, a liquid impervious backsheet joined with the topsheet, and an absorbent core positioned between the topsheet and the backsheet; a pair of side panels joined with the chassis assembly, the side panels extending laterally outwardly beyond the longitudinal edges of the chassis; and a closure system for maintaining the absorbent article on the wearer.

The side panels comprise a leg zone and a waist zone. The leg zone has an extension force which is less than the extension force of the waist zone. The lower extension force leg zone allows the side panels to easily expand with the leg movements of the wearer thereby reducing any red marking of the skin around the leg region. The higher extension force waist zone generates a continuous ring of tension about the wearer's waist providing improved initial and sustained fit.

In a particular embodiment, the side panels have a leg zone which is extensible in a direction having a vector component in the lateral direction, a waist zone which is extensible in a direction having a vector component in the lateral direction, the leg zone having an extension force less than an extension force of the waist zone, a separation zone separating the leg zone from the waist zone, the separation zone being non-extensible, and a grasping zone disposed laterally outwardly from the waist zone, the grasping zone being non-extensible.

In a further particular embodiment, the leg zone and the waist zone of each said side panel comprise a web material comprising at least a first region and a second region being comprised of the same material composition, the first region undergoing a substantially molecular level deformation and the second region initially undergoing a substantially geometric deformation when the web material is subjected to an applied elongation along at least one axis. In a still further embodiment, the leg zone of each side panel has an extension force between about 2 gm/cm and 10 gm/cm at 50% extension.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinence briefs, training pants, feminine hygiene garments, and the like.

Figure 1:
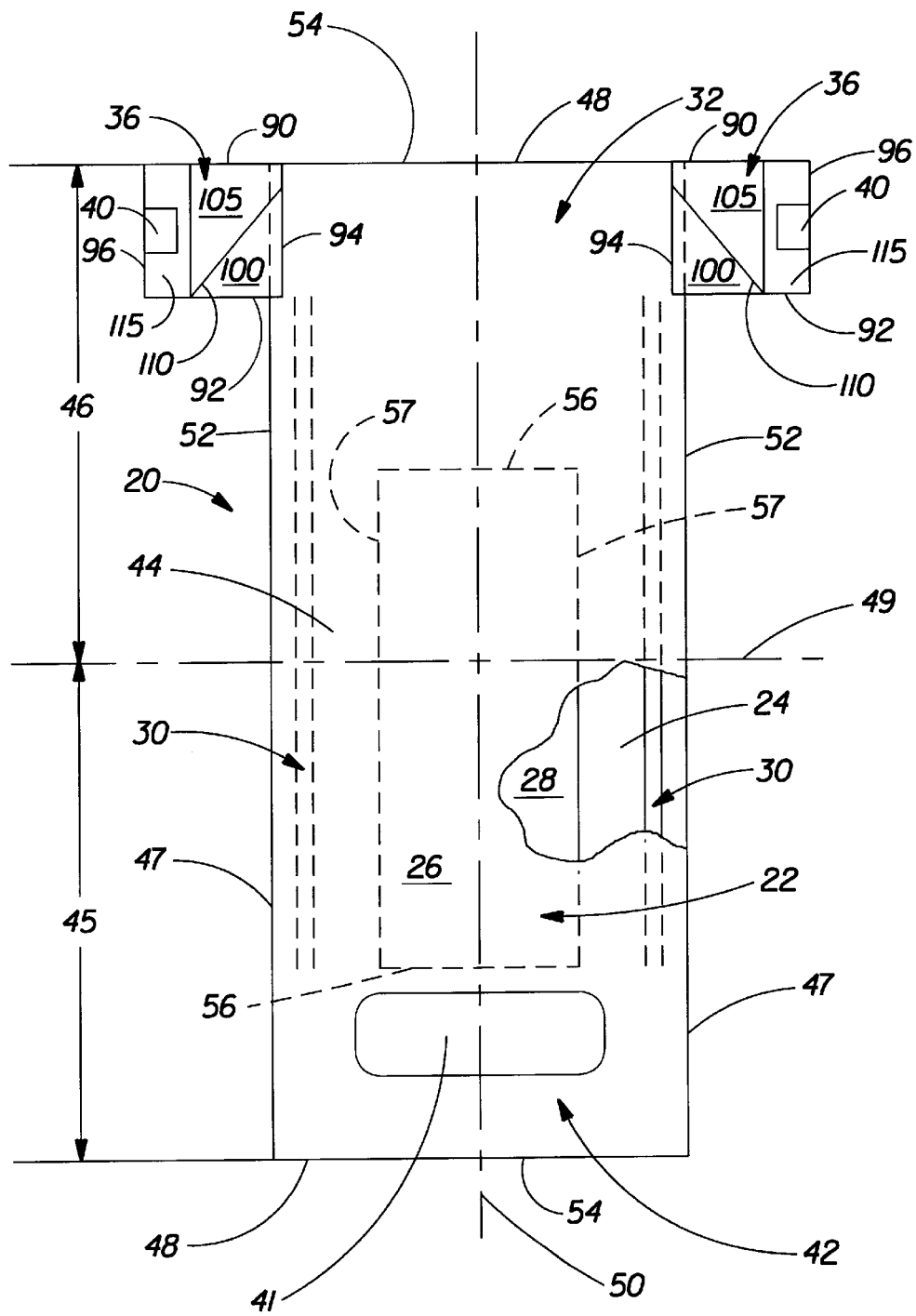
FIG. 1 is a plan view of a disposable diaper embodiment of the present invention having portions cut-away to reveal underlying structure, the outer surface of the diaper facing the viewer.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces away from the wearer, the outer surface, facing the viewer. As shown in FIG. 1, the diaper 20 has a generally "T-shape" and comprises a chassis assembly 22 preferably comprising a liquid pervious topsheet 24, a liquid impervious backsheet 26 joined with the topsheet 24, an absorbent core 28 positioned between the topsheet 24 and the backsheet 26; extensible leg cuffs 30; an extensible back waist feature 32; a pair of side panels 36; a closure system for fastening the diaper on the wearer preferably comprising at least a pair of fastening members 40 and a landing member 41; and an extensible front waist feature 42.

The diaper 20 of FIG. 1 has an inner surface (not shown), an outer surface 44 (facing the viewer in FIG. 1) opposed to the inner surface, a front waist region 45, a back waist region 46 opposed to the front waist region 45, and a periphery which is defined by the outer edges of the diaper 20 in which the longitudinal edges are designated 47 and the end edges are designated 48. (While the skilled artisan will recognize that a diaper is usually described in terms of having a pair of waist regions and a crotch region between the waist regions; in this application, for simplicity of terminology, the diaper 20 is described as having only waist regions, each of the waist regions including a portion of the diaper which would typically be designated as part of the crotch region). The inner surface of the diaper 20 comprises that portion of the diaper 20 which is positioned adjacent to the wearer's body during use (i.e., the inner surface generally is formed by at least a portion of the topsheet 24 and other components joined to the topsheet 24). The outer surface 44 comprises that portion of the diaper 20 which is positioned away from the wearer's body (i.e., the outer surface 44 generally is formed by at least a portion of the backsheet 26 and other components joined to the backsheet 26). The front waist region 45 and the back waist region 46 extend, respectively, from the end edges 48 of the periphery to the lateral centerline 49 of the diaper 20. (The lateral direction (x direction or width) is defined as the direction parallel to the lateral centerline 49 of the diaper 20; the longitudinal direction (y direction or length) being defined as the direction parallel to the longitudinal centerline 50; and the axial direction (Z direction or thickness) being defined as the direction extending through the thickness of the diaper 20.)

FIG. 1 shows a preferred embodiment of the diaper 20 in which the topsheet 24 and the backsheet 26 have length and width dimensions generally larger than those of the absorbent core 28. The topsheet 24 and the backsheet 26 extend beyond the edges of the absorbent core 28 to form portions of the periphery of the diaper. The periphery defines the outer perimeter or, in other words, the edges of the diaper 20. The periphery comprises the longitudinal edges 47 and the end edges 48.

The chassis assembly 22 (chassis panel) of the diaper 20 is shown in FIG. 1 as comprising the main body (chassis) of the diaper 20. The chassis assembly 22 comprises at least an absorbent core 28, preferably an outer covering layer comprising the topsheet 24 and the backsheet 26. Thus, the chassis assembly 22 comprises the main structure of the diaper with other features added to form the composite diaper structure. The chassis assembly 22 has a longitudinal edge 52 and an end edge 54. An exemplary example of a chassis assembly of the present invention is described in U.S. Pat. No. 3,860,003 issued to Kenneth B. Buell on Jan. 14, 1975, which patent is incorporated herein by reference.

The absorbent core 28 may be any absorbent means which is capable of absorbing and retaining liquids such as urine and other certain body exudates. The absorbent core 28 has a garment surface, a body surface, side edges 57, and waist or end edges 56. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including coform, cross-linked cellulose fibers, tissue including tissue wraps and tissue laminates, absorbent foams, absorbent sponges, superabsorbent polymers, absorbent gelling materials, or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the diaper 20. Further, the size and absorbent capacity of the absorbent core 28 may be varied to accommodate wearers ranging from infants through adults. FIG. 1 shows a preferred embodiment of the diaper 20 having a rectangular-shape absorbent core.

An absorbent structure useful as the absorbent core 28 of the present invention that has achieved wide acceptance and commercial success is described in U.S. Pat. No. 4,610,678 entitled "High-Density Absorbent Structures" issued to Weisman and Goldman on Sep. 9, 1986. U.S. Pat. No. 4,673,402 entitled "Absorbent Articles With Dual-Layered Cores" issued to Weisman, Houghton, and Gellert on Jun. 16, 1987; U.S. Pat. No. 4,888,231 entitled "Absorbent Core Having A Dusting Layer" issued to Angstadt on Dec. 19, 1989; U.S. Pat. No. 5,147,345 entitled "High Efficiency Absorbent Articles For Incontinence Management", issued to Young, LaVon & Taylor on Sep. 15, 1992; U.S. Pat. No. 5,102,597 entitled "Porous, Absorbent, Polymeric Macrostructures and Methods Of Making the Same", issued to Roe, Lahrman and Berg on Apr. 7, 1992; and U.S. Pat. No. 4,834,735, entitled "High Density Absorbent Members Having Lower Density and Lower Basis Weight Acquisition Zones", issued to Alemany and Berg on May 30, 1989; also describe absorbent structures that are useful in the present invention. The absorbent core 28 is preferably the dual-layer absorbent structure described in U.S. Pat. No. 5,234,423 entitled "Absorbent Article With Elastic Waist Feature and Enhanced Absorbency", issued to Alemany and Clear on Aug. 10, 1993. Each of these patents are incorporated herein by reference.

The backsheet 26 is positioned adjacent the garment surface of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola and Tucker on Mar. 4, 1986, and which is incorporated herein by reference. An exemplary attachment means of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, heat/pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mils).

Further, the backsheet may permit vapors to escape from the absorbent core (i.e., breathable while still preventing exudates from passing through the backsheet).

The topsheet 24 is positioned adjacent the body surface of the absorbent core 28 and is preferably joined thereto and to the backsheet 26 by attachment means (not shown) such as those well known in the art. Suitable attachment means are described with respect to joining the backsheet 26 to the absorbent core 28. As used herein, the term "joined" encompasses configurations whereby an element is directly secured to the other element by affixing the element directly to the other element, and configurations whereby the element is indirectly secured to the other element by affixing the element to an intermediate member(s) which in turn is affixed to the other element. In a preferred embodiment of the present invention, the topsheet 24 and the backsheet 26 are joined directly to each other in the diaper periphery and are indirectly joined together by directly joining them to the absorbent core 28 by the attachment means (not shown).

The topsheet 24 is compliant, soft feeling, and non-irritating to the wearer's skin. Further, the topsheet 24 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of a hydrophobic material to isolate the wearer's skin from liquids which have passed through the topsheet and are contained in the absorbent core 28 (i.e., to prevent rewet). If the topsheet is made of a hydrophobic material, at least the upper surface thereof is treated to be hydrophilic so that liquids will transfer through the topsheet more rapidly. This diminishes the likelihood that body exudates will flow off the topsheet rather than being drawn through the topsheet and being absorbed by the absorbent core. The topsheet can be rendered hydrophilic by treating it with a surfactant. Suitable methods for treating the topsheet with a surfactant include spraying the material with the surfactant and immersing the material in the surfactant. A more detailed discussion of such a treatment and hydrophilicity is contained in U.S. Pat. No. 4,988,344 entitled "Absorbent Articles With Multiple Layer Absorbent Layers" issued to Reising, et al. on Jan. 29, 1991.

There are a number of manufacturing techniques which may be used to manufacture the topsheet 24. For example, the topsheet 24 may be a nonwoven web of fibers. When the topsheet comprises a nonwoven web, the web may be spunbonded, carded, wet-laid, meltblown, hydroentangled, combinations of the above, or the like. A preferred topsheet is carded and thermally bonded by means well known to those skilled in the fabrics art. A preferred topsheet comprises staple length polypropylene fibers having a denier of about 2.2. As used herein, the term "staple length fibers" refers to those fibers having a length of at least about 15.9 mm (0.625 inches). Preferably, the topsheet has a basis weight from about 18 to about 25 grams per square meter.

The diaper 20 preferably further comprises extensible leg cuffs 30 for providing improved containment of liquids and other body exudates. Each extensible leg cuff 30 may comprise several different embodiments for reducing the leakage of body exudates in the leg regions. (The leg cuff can be and is sometimes also referred to as leg bands, leg flaps, barrier cuffs, or elastic cuffs.) U.S. Pat. No. 3,860,003 entitled "Contractable Side Portions For a Disposable Diaper", issued to Buell on Jan. 14, 1975, describes a disposable diaper which provides a contractible leg opening having a leg flap and one or more elastic members to provide an elasticized leg cuff (gasketing cuff). U.S. Pat. No. 4,909, 803 entitled "Disposable Absorbent Article Having Elasticized Flaps" issued to Aziz & Blaney on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. U.S. Pat. No. 4,704,115 entitled "Disposable Waste Containment Garment" issued to Buell on Nov. 3, 1987, discloses a disposable diaper or incontinent garment having side-edge-leakage-guard gutters configured to contain free liquids within the garment. U.S. Pat. No. 5,032,120 entitled "Disposable Absorbent Article Having Improved Leg Cuffs" issued to Freeland & Allen on Jul. 16, 1991, discloses an absorbent article having leg cuffs having a relatively low ultimate contact force at relatively high elongations accomplished, for example, by low contact force differential material. U.S. Pat. No. 5,087,255 entitled "Absorbent Article Having Inflected Barrier Cuffs" issued to Sims on Feb. 11, 1992, discloses an absorbent article having inflected barrier cuffs with the distal edge positioned outboard of the proximal edge in one waist region and inboard in the other to provide better fit about the hips/buttocks. Each of these patents are incorporated herein by reference.

The diaper 20 further comprises extensible waist features that provide improved fit and containment. The extensible waist features at least extend longitudinally outwardly from the chassis assembly, preferably a respective waist edge of the absorbent core 28, and generally form at least a portion of the end edge of the diaper 20. Thus, in the embodiment shown in FIG. 1, the extensible back waist feature 32 comprises that portion of the diaper 20 extending from the waist edge 56 of the absorbent core 28 in the back waist region 46 to the end edge 48 of the diaper 20. The waist feature can be constructed as a separate element joined to the chassis assembly 22 or as an extension of other elements of the diaper (i.e., unitary). Preferably, the waist feature is constructed as an extension of other elements of the chassis such as the backsheet 26, the topsheet 24, or both.

The extensible back waist feature 32 provides an extensible member that provides a more comfortable and contouring fit by initially conformably fitting the diaper to the wearer and sustaining this fit throughout the time of wear well past when the diaper has been loaded with exudates since the extensible back waist feature allows the diaper to expand and, preferably, to contract. Further, the extensible back waist feature develops and maintains wearing forces (tensions) that enhance the tensions developed and maintained by the closure system to maintain the diaper on the wearer and that enhance the fit of the diaper about the waist of the wearer. The extensible back waist feature further provides more effective application of the diaper since even if the diaperer pulls one side (side panel 36) of the extensible back waist feature farther than the other during application (asymmetrically), the diaper will "self-adjust" during wear.

The extensible back waist feature 32 may be constructed in a number of configurations and from a number of different materials. For example, the extensible back waist feature 32 may be elasticized by operatively joining an elastic member thereto such as the elasticized waistbands known in the art and as are disclosed in U.S. Pat. No. 4,515,595 issued to Kievit, et al. on May 7, 1985; and U.S. Pat. No. 5,151,092 issued to Buell, et al. on Sep. 29, 1992; each of which are incorporated herein by reference. Thus, the extensible back waist feature may be a stretch laminate such as a zero strain stretch laminate as is described in U.S. Pat. No. 5,151,092 Buell, et al. In a preferred embodiment of the present invention, the extensible back waist feature comprises a structural elastic-like film SELF web as described in U.S. Pat. No. 5,518,801 issued to Chappell et al. in May 21, 1996, which is incorporated herein by reference.

The web material of the present invention includes a strainable network having at least two distinct and dissimilar regions comprised of the same material composition. The first region is oriented substantially parallel to an axis of the elongation such that it will undergo a molecular-level deformation in response to an applied axial elongation in a direction substantially parallel to elongation axis before a substantial portion of the second region undergoes any substantial molecular-level deformation. As used herein, the term "substantially parallel" refers to an orientation between two axes whereby the subtended angle formed by the two axes or an extension of the two axes is less than 45°. In the case of a curvilinear element it may be more convenient to use a linear axis which represents an average of the curvilinear element. The second regions initially undergo a substantially geometric deformation in response to an applied elongation in a direction substantially parallel to the axis.

In the embodiment shown in FIG. 1, the side panels 36 are joined to the chassis assembly 22 such that they extend laterally outwardly from the longitudinal edges 52 of the chassis assembly. The side panels 36 may have a number of different sizes and shapes. In the preferred embodiment shown in FIG. 1, the side panels 36 have a rectangular shape. For a typical "large" (8 kg to 14 kg) baby diaper, the side panels may, for example, have a size of about 63 mm in the lateral direction by about 80 mm in the longitudinal direction.

The side panels 36 may be constructed in a number of configurations and from a number of different materials. The side panels may comprise conventional elastic materials or mechanically stretched laminates such as a zero strain stretch laminate. In a preferred embodiment of the present invention, the side panels comprise a SELF web as described in the aforementioned U.S. Pat. No. 5,518,801 issued to Chappell et al. FIGS. 2A and 2B show a SELF web forming zones of the side panel.

The side panels 36 may comprise a separate element affixed to the chassis assembly 22, or can be constructed as an extension of other elements of the diaper such as the backsheet 26 or the topsheet 24, preferably both the topsheet and the backsheet. In the embodiment of the present invention shown in FIG. 1, the side panels 36 each comprise a separate web joined to the chassis assembly 22. The side panels 36 are joined to the chassis assembly 22 in the back waist region 46 and extend laterally outwardly beyond the longitudinal edges 52. The side panels 36 comprise a first end edge 90, positioned adjacent and forming a portion of the end edge 48 of the diaper, a second end edge 92 positioned away from the first end edge 90 towards the lateral centerline 49, a first longitudinal edge 94, and a second longitudinal edge 96 positioned laterally outwardly from the longitudinal edge 52 of the chassis assembly 22. The first longitudinal edge 94 my be contiguous with the longitudinal edge 47, preferably the first longitudinal edge 94 is positioned laterally inwardly of the longitudinal edge 47.

The side panels 36 have a multiple zone construction comprising at least a leg zone 100 and a waist zone 105. The leg zone 100 is positioned adjacent to the longitudinal edge 52 of the chassis assembly 22. The waist zone 105 is positioned laterally outwardly from the leg zone 100. The leg zone 100 is extensible in a direction having a vector component in the lateral direction, preferably in the lateral direction. The waist zone 105 is extensible in a direction having a vector component in the lateral direction, preferably the lateral direction. The leg zone 100 is designed to have lower extension forces than the waist zone 105. The extension force of the leg zone 100 should be as low as possible. In a preferred embodiment, the extension force of the leg zone 100 is less than about 10 gm/cm, preferably less than about 5 gm/cm, at 50% extension. The leg zone of each side panel has an extension force between about 2 gm/cm and 10 gm/cm at 50% extension. The extension force of the waist zone is preferably between about 10 gm/cm to 30 gm/cm, preferably between about 15 gm/cm and 20 gm/cm, at 50% extension.

In the embodiment shown in FIG. 1, the leg zone 100 is separated from the waist zone 105 by a separation zone 110.

The separation zone 110 may be a line of demarcation distinguishing the leg zone 100 from the waist zone 105. Preferably, the separation zone 110 is a nonextensible zone which physically separates the leg zone 100 from the waist zone 105. The nonextensible separation zone 110 is preferably formed with the use of heat/pressure bonds, ultrasonic bonding or mechanical bonding which bonds the various layers of tile side panels together in such a way to render them nonextensible. The separation zone 110 may also be formed by joining additional materials to the side panel to render that portion nonextensible.

In the embodiment shown in FIG. 1, the leg zone 100, the waist zone 105, the separation zone 110, and the grasping zone 115 each comprise the same material. However, each zone has its own unique degree of force/extension. The use of a SELF web such as described in the aforementioned U.S. Pat. No. 5,518,801 issued to Chappell et al. allows the force/extension properties of each zone to be specifically designed.

The leg zone 100 may have a number of different sizes and shapes. In the preferred embodiment shown in FIG. 1, the leg zone 100 have a triangular shape. A side of the triangle forms a portion of the second end edge 92. The waist zone 105 may also have a number of different sizes and shapes. Preferably, the waist zone 105 has a triangular shape with a side of the triangle having a portion of the first end edge 90.

The leg zone 100 having the low force and unique triangular shape allows the side panel to expand with the leg movement of the wearer at relatively low forces. This provides the benefit of reduced red marking of the wearer's skin since less force lower tensions are riding along the leg of the wearer. The waist zone 105 maintains a continuous ring of high force in the waist area of the diaper which provides improved initial and sustained fit. This high force zone extends across the end edge 48 of the diaper providing the ring of tension necessary to initially fit and sustain this fit through use.

Figure 5:
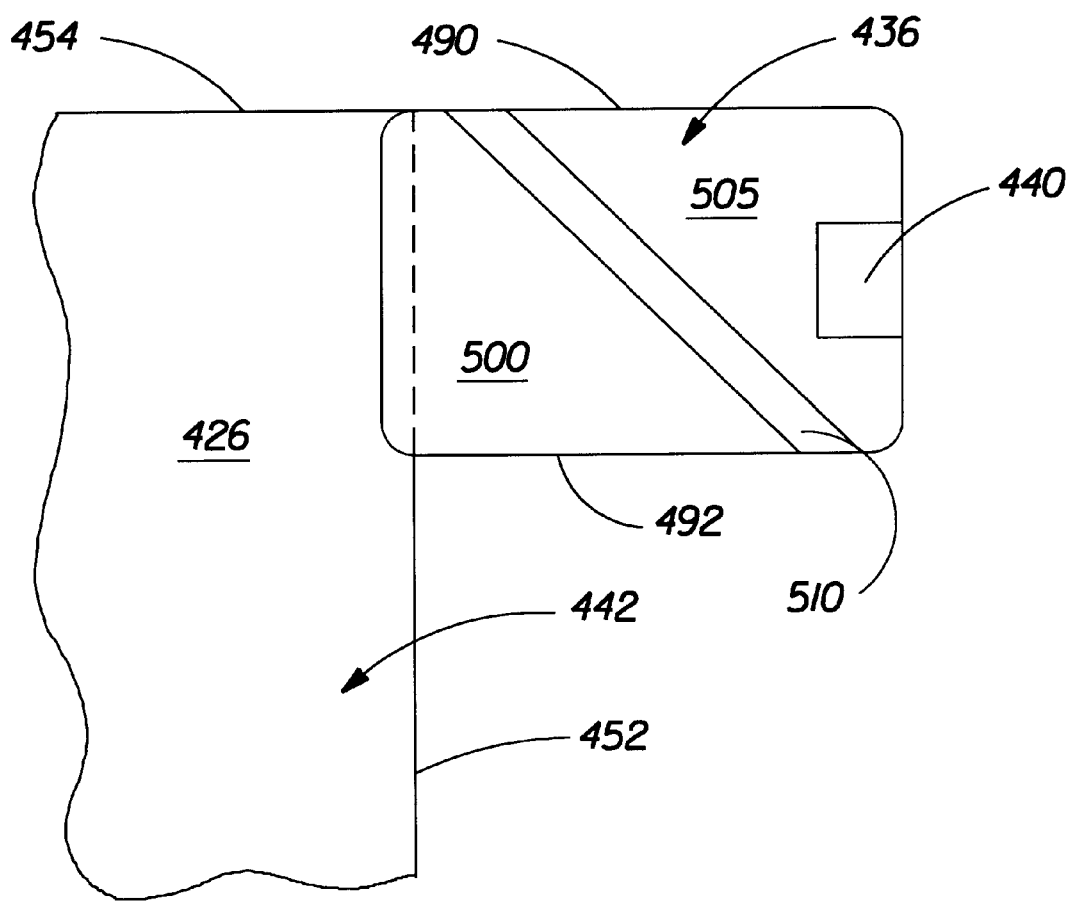
FIG. 5 is a fragmentary plan view of an alternative embodiment of a side panel of the present invention.

As shown in FIG. 1, the leg zone 100 preferably forms no portion of the first end edge 90 of the side panel 36. Preferably, the waist zone 105 forms no portion of the second end edge 92 of the side panel 36. Referring now to FIG. 5, there is shown an alternative embodiment of the side panel 436 of the present invention. Side panel 436 comprises a leg, zone 500, a waist zone 505 and a separation zone 510. The leg zone 500 forms a portion of both the first end edge 490 and the second end edge 492. The waist zone 505 forms a portion of both the first end edge 490 and the second end edge 492. Alternatively, the side panel 436 may be designed such that the leg zone 500 forms a portion of both the first end edge 490 and the second end edge 492 while the waist zone 505 forms a portion of the first end edge 490 but forms no portion of the second end edge 492. Alternatively, the side panel 436 may be designed such that the waist zone 505 forms a portion of both the first end edge 490 and the second end edge 492 while the leg zone 500 forms a portion of the second end edge 492 but forms no portion of the first end edge 490.

The side panels 36 may be joined to the chassis assembly 22 in a number of different ways as are known in the art including by adhesives, heat/pressure bonds, ultrasonic bonding, or mechanical bonding. Side panels 36 are preferably bonded to the chassis 22 via mechanical bonding indicated as 120 in FIG. 1.

Referring to FIG. 1, the side panels 36 preferably comprise a grasping region 115 disposed laterally outwardly from the waist zone 105. The grasping zone 115 is preferably a stiff material which is nonextensible and functions to allow for convenient grasping of the side panel 36 by the user to apply the fastening members 40 to the landing zone 41.

As shown in FIG. 1, the diaper 20 may also be provided with an extensible front waist feature 42. The extensible front waist feature 42 is designed to fit around the abdomen in the front waist of the wearer to improve the fit and containment of the diaper at the front waist. The extensible front waist feature 42 extends longitudinally outwardly from the chassis assembly 22, preferably the waist edge 56 of the absorbent core 28, and generally forms at least a portion of the end edge 48 of the diaper 20 in the front waist region 45. The extensible front waist feature 42 may comprise any of the known configurations of an elastic feature or any of the extensible features as described herein. For example, the extensible front waist feature may comprise any of the elasticized waistbands as are known in the art such as are disclosed in the above-referenced U.S. Pat. No. 4,515,595 (Kievit, et al.) and U.S. Pat. No. 5,151,092 (Buell, et al.). Further, the extensible front waist feature may comprise a stretch laminate such as a zero strain stretch laminate as is described in U.S. Pat. No. 5,151,092 (Buell, et al.).

The diaper 20 is also provided with a closure system for fitting the diaper on the wearer. While the closure system may take on a number of configurations such as adhesive tape tabs, mechanical closure tape tabs, fixed position fasteners, side seams as for training pants, or any other closure means as are known in the art; as shown in FIG. 1, the closure system preferably comprises an adhesive tape tab fastening system including a pair of tape tab fastening members 40 and a landing member, preferably a reinforcing strip 41 as in FIG. 1 or, the alternative, a portion of the backsheet, positioned in the front waist region 45 of the diaper 20. Examples of suitable adhesive tape tab fastening systems are disclosed in U.S. Pat. No. 3,848,594 issued to Buell on Nov. 19, 1974; and U.S. Pat. No. 4,662,875 issued to Hirotsu and Robertson on May 5, 1987; each of which are incorporated herein by reference. Examples of other closure systems, including mechanical closure systems, useful in the present invention, are disclosed in U.S. Pat. No. 4,869,724 issued to Scripps on Sep. 26, 1989; U.S. Pat. No. 4,848,815 issued to Scripps on Jul. 11, 1989; and the two-point fastening system described in U.S. Pat. No. 5,242,436 issued to Weil, Buell, Clear, and Falcone on Sep. 7, 1993; each of which are incorporated herein by reference.

The diaper 20 is preferably applied to a wearer by positioning the back waist region 46 under the wearer's back and drawing the remainder of the diaper between the wearer's legs so that the front waist region 45 is positioned across the front of the wearer. The tab portions of the tape tabs 40 are then released from the release portion. The diaperer then wraps the side panel 36 around the wearer, while still grasping the tab portion. The side panel will typically be extended and tensioned during this operation so as to conform to the size and shape of the wearer. The tape tab 40 is secured to the reinforcing strip 41, the landing member, on the chassis assembly 22 to effect a side closure. The process is then repeated with the other tape tab. Thus, the diaper is closed on the wearer and the extensible back waist feature and the other elements, if provided, provide the fit and containment benefits as described herein. Alternatively, the diaper may be fastened prior to being fitted on the wearer such that it may be used as a pant. In either configuration, the pant or diaper may be removed by disengaging the fasteners or removing it as one would a pant.

Figure 2:
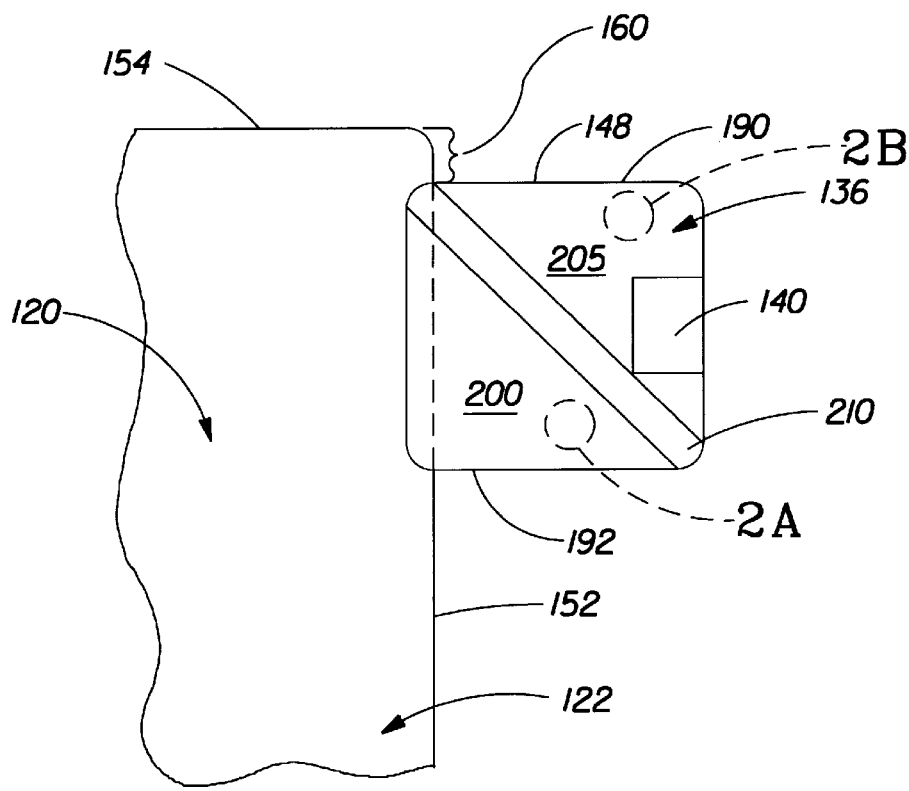
FIG. 2 is a fragmentary plan view of an alternative embodiment of a side panel of the present invention.
Figure 2A:
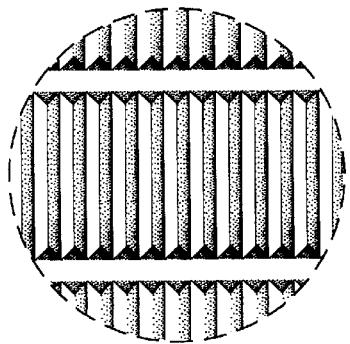
FIG. 2A is an exploded view of the region 2A shown in FIG. 2.
Figure 2B:
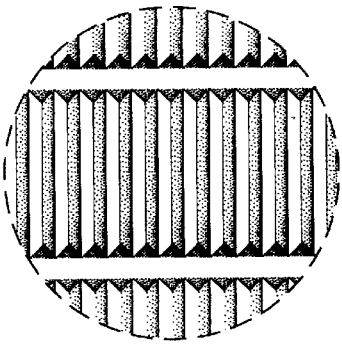
FIG. 2B is an exploded view of the region 2B shown in FIG. 2.

FIG. 2 shows an alternative embodiment of a side panel 136 of the present invention. Side panel 136 is a separate member joined to the chassis assembly 122. The side panels 136 extends laterally outwardly beyond the longitudinal edge 152 of the chassis assembly 122. The side panel 136 comprises a leg zone 200, a waist zone 205, and a separation zone 210. The fastening member is joined to the waist zone as the side panel 136 does not include a grasping zone. The leg zone 200 has a triangular shape where a side of the triangle forms a substantial portion of the second end edge 192. The waist zone 205 has a triangular shape where a side of the triangle forms a substantial portion of the first end edge 190. The side panel is joined to the chassis assembly 122 such that it is spaced away from the end edge 152 of the chassis assembly 122. The first end edge 190 is spaced away from the end edge 154 a distance indicated as 160. Distance 160 is less than about 2 cm, preferably less than about 1 cm. The first end edge 190 of the side panel 136 forms a portion of the end edge 148 of the diaper 120.

Figure 3:
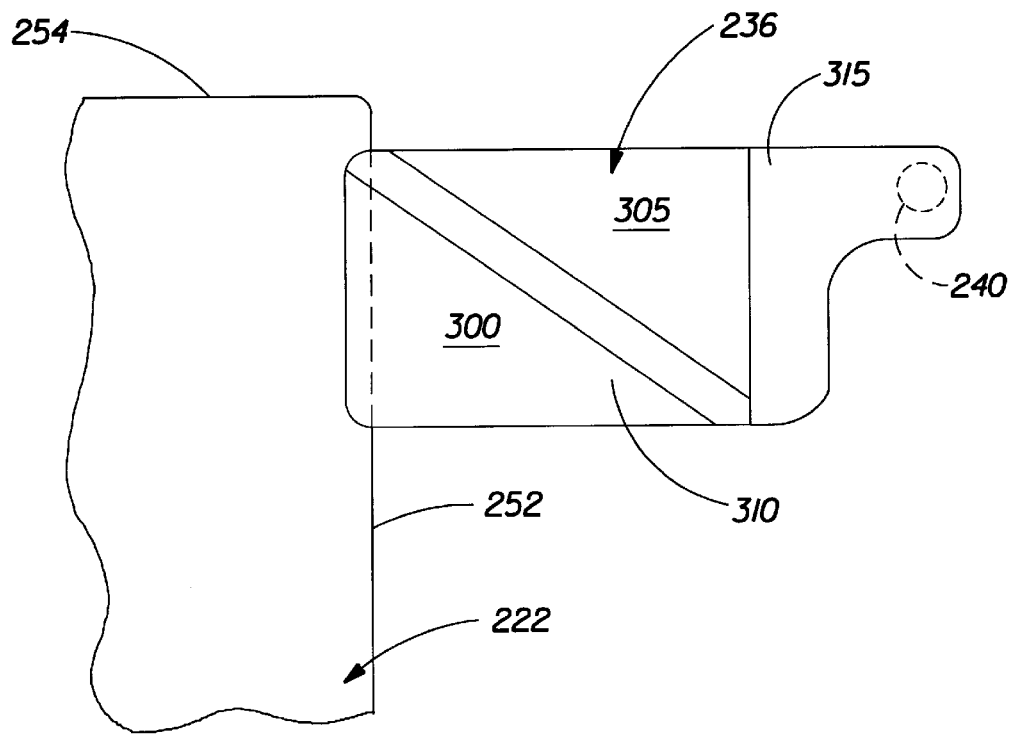
FIG. 3 is a fragmentary plan view of an alternative embodiment of a side panel of the present invention.

FIG. 3 shows an alternative embodiment of a side panel 236 of the present invention. The side panel 236 is a separate member joined to the chassis assembly 222. The chassis assembly 222 has a longitudinal edge 252 and an end edge 254. The side panel 236 is a separate member joined to the chassis assembly 222. The side panel 236 extends laterally outwardly beyond the longitudinal edge 252 of the chassis assembly 222. The side panel 236 comprises a leg zone 300, a waist zone 305, a separation zone 310, and a grasping zone 315. The grasping zone 315 and the separation zone 310 are preferably nonextensible zones. The fastening member 240 preferably comprises a mechanical closure member. Mechanical closure members may comprise any well known means for achieving a closure by mechanical engagement such as hook and loop fastening materials. When the fastening member comprises a mechanical closure member, the landing members (not shown in FIG. 3) comprises a complementary mechanical closure element which is engageable with the fastening member 240.

Figure 4:
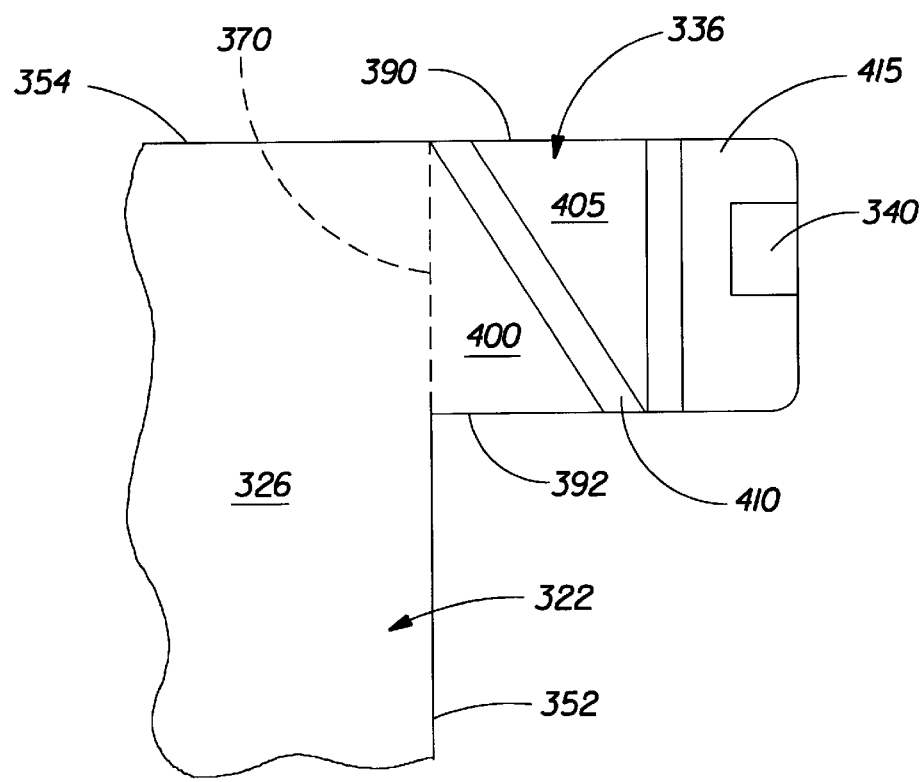
FIG. 4 is a fragmentary plan view of an alternative embodiment of a side panel of the present invention.

FIG. 4 shows an alternative embodiment of a side panel 336 of the present invention. Side panel 336 is an extension of the backsheet 326 and the topsheet (not shown) with other elements, such as elastic members, joined thereto, preferably between the topsheet and backsheet. The side panel 336 comprises a leg zone 400, a waist zone 405, a separate zone 410, and a grasping zone 415. In the embodiment of FIG. 4, the first end edge 390 is contiguous with the end edge 354 of the chassis assembly 322 such that it forms a continuous edge across the back waist region. The second end edge 392 is non-parallel to the first end edge 390. The first end edge 390 extends parallel to the lateral centerline of the diaper while the second end edge 392 extends at an angle to the lateral centerline. A line 370 defines the boundary between the side panel 336 and the chassis assembly 322. In this embodiment the line 370 is an extension of the longitudinal edges 352 of the chassis assembly 322. However, line 370 may be positioned laterally inwardly or laterally outwardly from the longitudinal edge 352.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article having a longitudinal centerline, a longitudinal direction defined as the direction parallel to said longitudinal centerline, a lateral centerline perpendicular to said longitudinal centerline, a lateral direction defined as the direction parallel to said lateral centerline, a front waist region and a back waist region, the absorbent article further comprising:

a chassis assembly having end edges and longitudinal edges, said chassis assembly comprising a liquid pervious topsheet, a liquid impervious backsheet joined with said topsheet, and an absorbent core positioned between said topsheet and said backsheet; and a pair of side panels joined with said chassis assembly, said side panels extending laterally outwardly beyond said longitudinal edges, each said side panel having a leg zone which is extensible in a direction having a vector component in the lateral direction, a waist zone which is extensible in a direction having a vector component in the lateral direction, the leg zone having an extension force less than an extension force of the waist zone, a separation zone separating said leg zone from said waist zone, said separation zone being non-extensible, and a grasping zone disposed laterally outwardly from said waist zone, said grasping zone being non-extensible.

2. The absorbent article of claim 1 wherein said leg zone of each said side panel has an extension force between about 2 gm/cm and 10 gm/cm at 50% extension.

3. The absorbent article of claim 2 wherein said waist zone of each said side panel has an extension force between about 10 gm/cm and 30 gm/cm at 50% extension.

4. The absorbent article of claim 1 or 2 wherein said leg zone and said waist zone of each said side panel comprise a web material comprising at least a first region and a second region being comprised of the same material composition, said first region undergoing a substantially molecular level deformation and said second region initially undergoing a substantially geometric deformation when said web material is subjected to an applied elongation along at least one axis.

5. The absorbent article of claim 1 wherein said leg zone of each said side panel has a triangular shape.

6. The absorbent article of claim 5 wherein said waist zone of each said side panel has a triangular shape.

7. A disposable absorbent article having a longitudinal centerline, a longitudinal direction defined as the direction parallel to said longitudinal centerline, a lateral centerline perpendicular to said longitudinal centerline, a lateral direction defined as the direction parallel to said lateral centerline, a front waist region and a back waist region, the absorbent article further comprising:

a chassis assembly having end edges and longitudinal edges, said chassis assembly comprising a liquid pervious topsheet, a liquid impervious backsheet joined with said topsheet, and an absorbent core positioned between said topsheet and said backsheet; and a pair of side panels joined with and extending laterally outwardly from the longitudinal edges of said chassis assembly, each said side panel having a rectangular shape, a leg zone which has a triangular shape and is extensible in a direction having a vector component in the lateral direction, a waist zone which has a triangular shape and is extensible in a lateral direction having a vector component in the lateral direction, and the leg zone having an extension force less than an extension force of the waist zone.

8. The absorbent article of claim 7 wherein each said side panel is a separate member joined with said chassis assembly.

9. The absorbent article of claim 7 wherein each of said side panels is an extension of said topsheet and said backsheet.

10. The absorbent article of claim 9 wherein said leg zone and said waist zone of each said side panel each comprises a web material comprising at least a first region and a second region being comprised of the same material composition, said first region undergoing a substantially molecular level deformation and said second region initially undergoing a substantially geometric deformation when said web material is subjected to an applied elongation along at least one axis.

11. The absorbent article of claim 7 wherein said leg zone and said waist zone of each said side panel each comprises a web material comprising at least a first region and a second region being comprised of the same material composition, said first region undergoing a substantially molecular level deformation and said second region initially undergoing a substantially geometric deformation when said web material is subjected to an applied elongation along at least one axis.

12. The absorbent article of claim 7 wherein each said side panel has a separation zone formed from the group consisting of heat/pressure bonds, ultrasonic bonds, mechanical bonds, or the joinder of additional materials.

13. A disposable absorbent article having a longitudinal centerline, a longitudinal direction defined as the direction parallel to said longitudinal centerline, a lateral centerline perpendicular to said longitudinal centerline, a lateral direction defined as the direction parallel to said lateral centerline, a front waist region and a back waist region, the absorbent article further comprising:

a chassis assembly having end edges and longitudinal edges, said chassis assembly comprising a liquid pervious topsheet, a liquid impervious backsheet joined with said topsheet, and an absorbent core positioned between said topsheet and said backsheet; and a pair of rectangular side panels comprising a separate material joined with said chassis assembly, said side panels extending laterally outwardly beyond said longitudinal edges, each said side panel having a first end edge, a second end edge, a leg zone which has a triangular shape and is extensible in a direction having a vector component in the lateral direction;

a waist zone which has a triangular shape and is extensible in a direction having a vector component in the lateral direction, the leg zone having an extension force less than an extension force of the waist zone, said leg zone and said waist zone each comprising a web material comprising at least a first region and a second region being comprised of the same material composition, said first region undergoing a substantially molecular level deformation and said second region initially undergoing a substantially geometric deformation when said web material is subjected to an applied elongation along at least one axis, a separation zone separating said leg zone from said waist zone, said separation zone being non-extensible, said separation zone extending diagonally from said first end edge to said second end edge and a grasping zone disposed laterally outwardly from said waist zone, said grasping zone being non-extensible.

14. The absorbent article of claim 13 wherein said leg zone of each said side panel has an extension force between about 2 gm/cm and 10 gm/cm at 50% extension and said waist zone of each said side panel has an extension force between about 10 gm/cm and 30 gm/cm at 50% extension.

15. The absorbent article of claim 14 wherein a side of the triangle forming said waist zone of each said side panel forms said first end edge.

16. The absorbent article of claim 15 wherein said separation zone of each said side panel is formed from the group consisting of heat/pressure bonds, ultrasonic bonds, mechanical bonds, or the joinder of additional materials.

* * * * *